United States Patent [19]

Renneker

[11] Patent Number: 5,038,601
[45] Date of Patent: Aug. 13, 1991

[54] APPARATUS FOR TESTING FRICTION TORQUE TRANSMITTING DEVICES

[75] Inventor: Craig M. Renneker, Royal Oak, Mich.

[73] Assignee: General Motors Corporation, Detroit, Mich.

[21] Appl. No.: 567,482

[22] Filed: Aug. 15, 1990

[51] Int. Cl.$^5$ ............................................. G01N 19/02
[52] U.S. Cl. ........................................................... 73/9
[58] Field of Search .......................... 73/7, 9, 10, 118.1, 73/121

[56] References Cited
U.S. PATENT DOCUMENTS
3,208,266 9/1965 Black ........................................ 73/9

Primary Examiner—Robert Raevis
Attorney, Agent, or Firm—Donald F. Scherer

[57] ABSTRACT

A friction disc test machine has a cavity in which alternately spaced stationary and rotary friction discs are disposed. The friction discs are urged into engagement by a selectively actuatable fluid operated piston to bring the rotating discs to a halt. An end cover and balance reaction piston are provided to limit the axial disc movement. The balance reaction piston is slidably disposed in a cavity formed in the end cover for linear and angular movement relative thereto. One friction disc abuts the balance piston whereby, due to the alignment properties of the piston, all of the friction discs are maintained in parallel alignment during engagement therebetween.

3 Claims, 2 Drawing Sheets

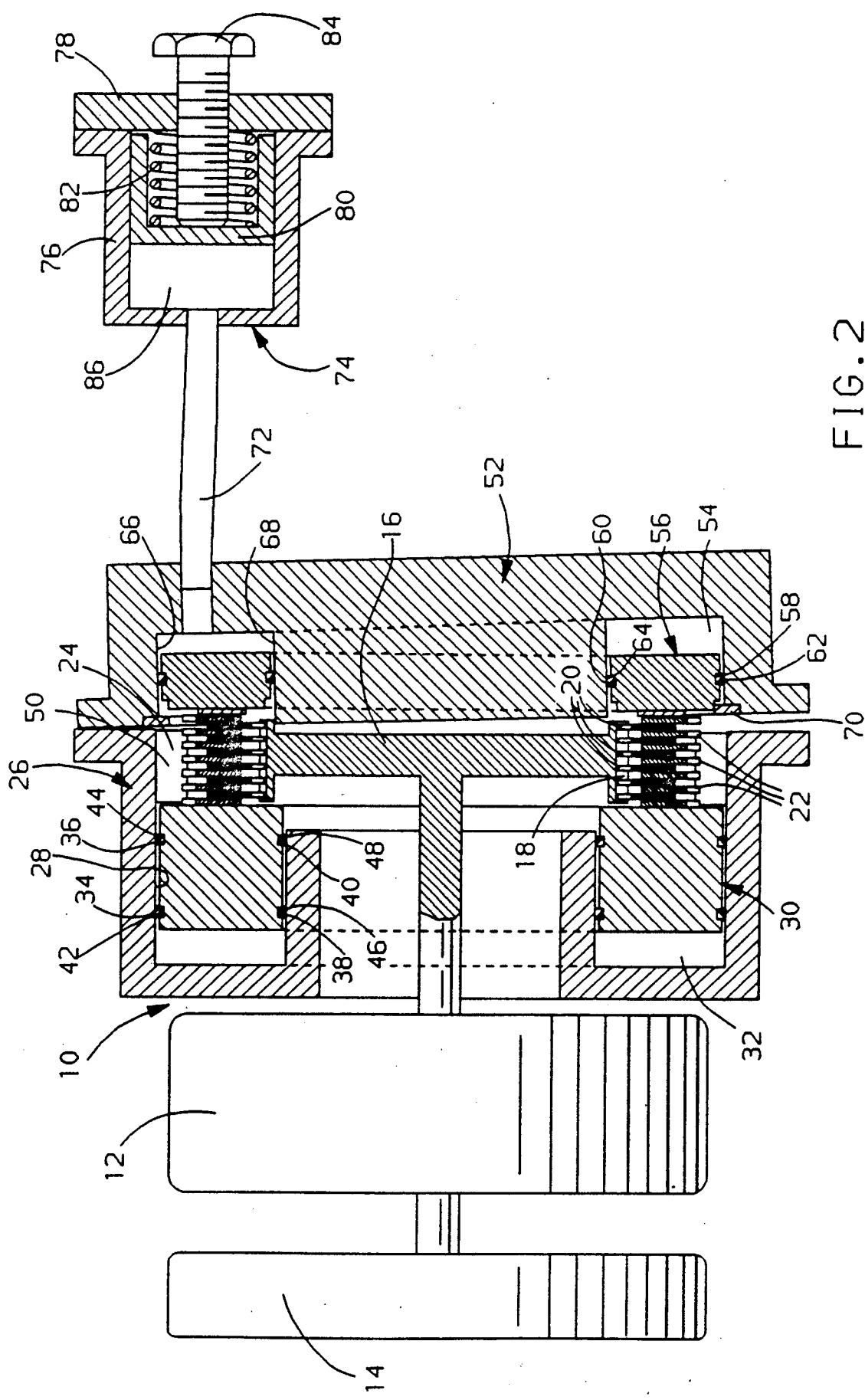

APPARATUS FOR TESTING FRICTION TORQUE TRANSMITTING DEVICES

BACKGROUND OF THE INVENTION

This invention relates to test machines, and more particularly, to machines for testing the friction characteristics of torque transmitting friction devices.

It is desirable to test friction disc clutch packs, such as those used in automotive transmissions to determined their durability and friction characteristics. Such testing is accomplished by a machine that is commonly termed an SAE #2 Clutch Test Machine. These machines are comprised of an electric motor which is drivingly connected to an inertia load and one set of plates for the disc pack. The other set of discs are restrained from rotation in a housing. The housing is closed by an end cover which serves as a support surface for the friction discs upon engagement by a selectively actuatable piston disposed in the housing.

To conduct the tests on the friction disc pack, the electric motor is rotated at a predetermined speed thereby causing the inertia disc and the rotary portion of the friction disc pack to rotate at that speed. The electric motor is then de-actuated and the friction pack is forced into engagement by the piston causing the rotating discs, the inertia disc and the electric motor to come to a halt.

While the disc pack is being engaged, instruments are utilized to measure various characteristics, such as time, torque transmitted and speed. These performance characteristics can be utilized to determine the operating and friction characteristics of the disc pack. To determine the durability or effective life of a disc pack, a repeatable cycle is imposed on the SAE #2 Machine, such that the disc pack is alternately brought to an operating speed, after which the disc pack is engaged the the system is brought to a halt. This cycle is repeated for a predetermined number of times, after which the friction characteristics of the disc pack are again tested or measured, and the disc pack is visually inspected.

It has been found that the end cover of the test machine can be slightly misaligned during assembly of the disc pack, such that the load imposed by the engaging piston will not be uniform about the periphery of the friction discs. This can lead to reduced operating life and incorrect frictional characteristic calculations. The test machine is designated as a clutch test machine, however, it will provide testing for disc type brake members which are utilized in automatic transmissions also.

SUMMARY OF THE INVENTION

It is an object of the present invention to provide an improved friction disc test machine having a body end cover, wherein a disc assembly is disposed within the body and the end cover has disposed therein a compensating balance piston which has sufficient freedom to adjust for misalignment of the end cover on the body to ensure parallelism between the friction discs.

It is another object of this invention to provide an improved friction disc test apparatus, wherein a plurality of friction discs are aligned in a cavity within a housing which is closed at one end by an end cover, and further wherein, a piston is slidably disposed in a fluid filled cavity in the end cover which cavity is connected with an accumulator in a manner to permit the piston to assume parallel alignment with the friction discs, regardless of any misalignment between the end cover and housing.

These and other objects and advantages of the present invention will be more apparent from the following description and drawings.

DESCRIPTION OF THE DRAWINGS

FIG. 2 is a representation similar to FIG. 1 showing the end cover of the test machine to be misaligned.

DESCRIPTION OF AN EXEMPLARY EMBODIMENT

Figure 1:
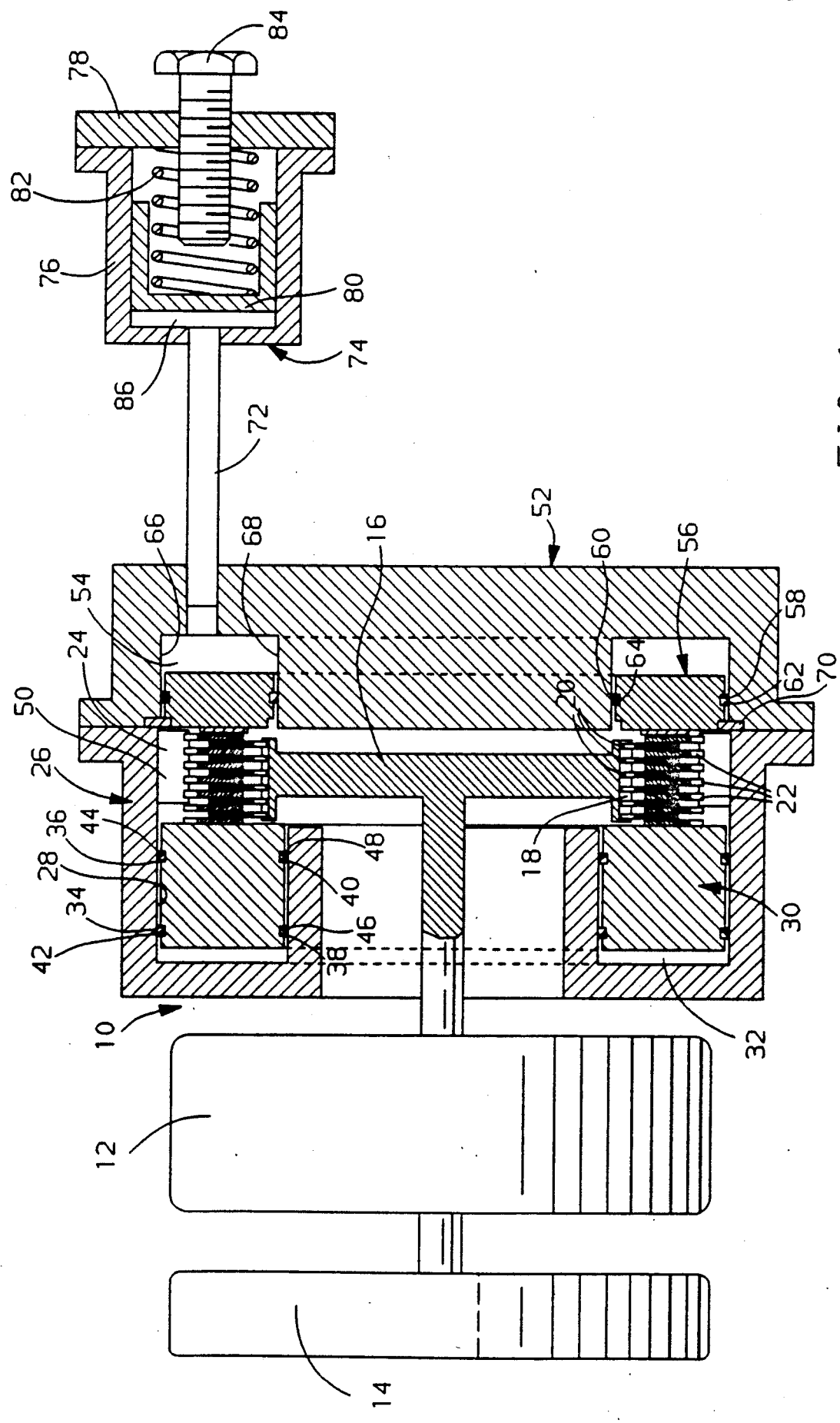
FIG. 1 is a diagrammatic representation of a test machine incorporating the present invention.

Referring to the drawings, there is seen in FIGS. 1 and 2 an apparatus or test machine for testing the characteristics of a friction torque transmitting device, such as a clutch or brake, and generally designated 10. This test machine includes an electric drive motor 12 which is drivingly connected to an inertia flywheel 14 and a disc input member 16. The inertia flywheel 14 and disc input member are both rotatable with the electric motor 12.

The disc input member has a spline or drive connection 18 to which is splined a plurality of friction discs 20. These friction discs 20 are alternately spaced with friction discs 22 which are splined at their outer diameter to a stationary support spline 24 formed in a stationary housing 26. The housing 26 also has formed therein, a cavity 28 in which is slidably disposed an annular piston 30 which cooperates with the cavity 28 to define an apply chamber 32. The piston 30 has four annular seal grooves 34, 36, 38 and 40, in which are disposed respective seal members 42, 44, 46 and 48. These seals 42-48 cooperate with the axial walls of the cavity 28 to prevent leakage between the apply chamber 32 and the atmosphere.

The apply chamber 32 is preferably connected to a pneumatic supply source, not shown, through a selectively operable control device of conventional manufacture, which is also not shown. The friction discs 20 and 22 are disposed in a cavity 50 which is closed by an end cover 52. The end cover 52 is secured to the stationary housing 26 by any conventional manner, such as clamps or screws. The end cover 52 has formed therein a reaction chamber or cavity 54, in which is slidably disposed an annular reaction or balance piston 56. The balance piston 56 has formed thereon a pair of annular seal grooves 58 and 60, in which are disposed annular seals 62 and 64, respectively. The annular seals 62 and 64 are preferably of the lip seal type which will permit sufficient clearance between the axial walls 66 and 68 of the reaction chamber 54, so that the annular reaction piston 56 can be canted within the reaction chamber 54, thereby remaining parallel to the friction discs 20 and 22 which are disposed in the cavity 50.

Secured in the end cover 52 is a stop ring 70 which limits the leftward axial movement of the piston 56 in the chamber 54. The chamber 54 is preferably filled with hydraulic fluid and is in fluid communication through a passage 72 with an accumulator 74. The accumulator 74 includes a housing 76, an end cover 78, a piston 80, a return spring 82 and a stop member 84. The piston 80 and housing 76 cooperate to form a chamber 86 which is in fluid communication with the passage 72.

When the piston 30 is actuated and the friction discs 20 and 22 are brought into frictional engagement, the annular reaction piston 56 will move slightly rightward in the reaction chamber 54, while serving as a reaction or braking member for the disc pack. The movement of the piston 56 causes the transfer of hydraulic fluid from the reaction chamber 54 to the chamber 86 of the accumulator 74, thereby causing movement of the piston 80 against the spring 82. The piston 80 will move rightward against the spring 82 permitting the chamber 86 to increase in volume until the piston 80 abuts the stop member 84. At this point, the pressure in reaction chamber 54 will be raised significantly and the clutch pack, comprised of the discs 20 and 22, will be fully engaged.

The test machine 10, which in FIG. 2, depicts the end cover 52 in misalignment with the housing 26. The misalignment has been exaggerated to depict the repositioning of the reaction piston 56 that can occur. In reality, the end cover 52 will only be a few one hundredths of an inch out of alignment, however, this amount of misalignment will be sufficient to create discrepancies in the test results. As shown in FIG. 2, the piston 56 will be canted in the reaction chamber 54 so as to maintain parallel alignment with the friction discs 20 and 22 disposed in the cavity 50. The friction discs 20 and 22 will be brought into engagement with the friction surfaces substantially parallel and the reaction surfaces will be equally distributed about the surfaces thereof.

During operation of the test machine, the drive motor 12 is brought up to a predetermined speed, for example, 1800 rpm, and then deactivated. Simultaneously, the piston 30 is actuated causing the friction engagement between the discs 20 and 22. Since the discs 22 cannot rotate, the inertia flywheel 14 will be brought to a halt, thereby imposing a reaction load between the friction disc members which will result in the generation of heat. To simulate the operating environment of the friction discs 20 and 22, the cavity 50 has hydraulic fluid disposed therein. This fluid provides lubrication and cooling for the friction discs during the engagement period similar to the reaction that occurs in a power transmission.

As previously mentioned, the disc pack, comprised of discs 20 and 22, can be either a clutch or a brake. The fact that the discs are brought to a halt during engagement is inconsequential since during operation, the adjacent discs of a clutch pack are brought to conjoint rotation, and the frictional characteristics are not affected by whether the disc pack is rotating or stationary after full engagement occurs.

The inertia disc 14, as well as the inertia load supplied by the drive motor 12, must be consistent with the inertia loading that the disc pack will be subjected to during actual operation in a transmission. Generally during engagement, a friction clutch will have to absorb the inertia load due to the engine and torque converter of a transmission and the rotating gears within the transmission. The friction brake on the end must accommodate the acceleration or deceleration of the engine and torque converter by transmitting the reaction torque to ground during a ratio interchange. In other words, the inertia loading imposed on a friction device during shifting is represented by the inertia flywheel and drive motor of the friction test machine 10.

The embodiments of the invention in which an exclusive property or privilege is claimed are defined as follows:

1. An improvement in fluid operated friction torque transmitting test apparatuses having a drive motor coupled with an inertia load and an input member, a stationary housing comprising a selectively actuatable fluid operated piston, a disc cavity and stationary support members; a plurality of first friction discs drivingly connected with the input member for conjoint rotation therewith and being disposed in the disc cavity; a plurality of second friction discs disposed in the disc cavity and being drivingly connected with the stationary support members and being interleaved with the first friction discs for frictional engagement therewith when said piston is actuated; and an end cover means for closing one end of the disc cavity; wherein the improvement comprises: an annular fluid cavity formed in said end cover means; annular balance piston slidably disposed in said fluid cavity for parallel alignment with one of said first and second friction discs; fluid accumulator means in fluid communication with said fluid cavity for permitting said balance piston to move in said cavity whereby the volume of said cavity is changed; stop ring secured in said end cover for limiting the movement of said balance piston; and hydraulic fluid in said fluid cavity, said balance piston being movable to compensate for misalignment between said end cover and said stationary housing for ensuring that said first and second friction discs will be urged into mutual parallel contact upon actuation of said fluid operated piston.

2. The test apparatus defined in claim 1, wherein said accumulator means is disposed to accept hydraulic fluid discharge from said fluid cavity to accommodate movement of said balance piston.

3. The test apparatus defined in claim 2, and further wherein said accumulator means includes stop means for limiting the hydraulic fluid discharged from the fluid cavity means.

* * * * *